(12) United States Patent
Frazee et al.

(10) Patent No.: US 10,402,839 B1
(45) Date of Patent: Sep. 3, 2019

(54) METHODS AND SYSTEMS FOR DETERMINING DRUG TREND AND DRUG INFLATION

(71) Applicant: Express Scripts, Inc., St. Louis, MO (US)

(72) Inventors: Sharon Glave Frazee, O'Fallon, MO (US); Robert F. Nease, Jr., St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 502 days.

(21) Appl. No.: 13/860,002

(22) Filed: Apr. 10, 2013

Related U.S. Application Data

(60) Provisional application No. 61/622,506, filed on Apr. 10, 2012.

(51) Int. Cl.
*G06Q 30/02* (2012.01)
*G06Q 50/22* (2018.01)
*G16H 50/70* (2018.01)

(52) U.S. Cl.
CPC ......... *G06Q 30/0206* (2013.01); *G06Q 50/22* (2013.01); *G16H 50/70* (2018.01)

(58) Field of Classification Search
CPC ........ G06Q 50/22; G06Q 50/24; G06Q 30/00; G06Q 30/02; G06Q 30/0201; G06Q 30/0202; G06Q 30/0206; G06Q 40/00; G06Q 90/00; G06F 19/322; G06F 19/327; G06F 19/30; G06F 19/326; G06F 19/36; G16H 10/00; G16H 10/60; G16H 15/00; G16H 40/00; G16H 40/20; G16H 40/40; G16H 40/60; G16H 40/63; G16H 40/67; G16H 50/00; G16H 50/70
USPC ........................................................ 705/2, 3
See application file for complete search history.

(56) References Cited

U.S. PATENT DOCUMENTS

| 6,195,612 B1 * | 2/2001 | Pack-Harris .......... G06F 19/328 702/2 |
| 7,509,263 B1 * | 3/2009 | Fiedotin ................ G06F 19/324 348/516 |
| 8,374,907 B1 * | 2/2013 | Choi ...................... G06Q 30/02 705/1.1 |

(Continued)

OTHER PUBLICATIONS

A. Aizcorbe and N. Nestoriak, "Price indexes for drugs: A review of the issues," Bureau of Economic Analysis, BEA Working Papers, 2010, 35 pages. Available at: http://econpapers.repec.org/paper/beawpaper/0050.htm.*

(Continued)

*Primary Examiner* — Jason S Tiedeman
(74) *Attorney, Agent, or Firm* — Tucker Arensberg, P.C.

(57) ABSTRACT

Methods and systems for determining drug trend and drug inflation are described. In one embodiment, an index sample may be selected including an identification of a plurality of drugs. A weighting factor associated with each of the plurality of drugs in the index sample may be calculated. A first weighted price of for the plurality of drugs may be calculated for a first time period. A second weighted price for the plurality of drugs may be calculated for a second time period. A price index may be calculated for the second time period based on the first weighted price and the second weighted price. Other methods and systems are described.

21 Claims, 8 Drawing Sheets

(56) References Cited

U.S. PATENT DOCUMENTS

| | | | | |
|---|---|---|---|---|
| 2002/0133375 A1* | 9/2002 | Moore | ............ | G06F 19/327 705/2 |
| 2006/0212318 A1* | 9/2006 | Dooley | ............ | G06Q 10/10 705/4 |
| 2007/0233516 A1* | 10/2007 | Howe | ............ | G06F 19/328 705/2 |
| 2008/0120165 A1* | 5/2008 | Yan | ............ | G06Q 30/02 705/342 |
| 2008/0183492 A1* | 7/2008 | Warren | ............ | G06Q 10/10 705/2 |
| 2009/0083334 A1* | 3/2009 | Smith | ............ | G06Q 10/10 |
| 2009/0313039 A1* | 12/2009 | Cedergreen | ............ | G06Q 30/02 705/2 |
| 2010/0004945 A1* | 1/2010 | Petratos | ............ | G06F 19/328 705/2 |
| 2011/0060603 A1* | 3/2011 | Capelli | ............ | G06Q 10/10 705/2 |
| 2011/0119207 A1* | 5/2011 | Tong | ............ | G06F 19/328 705/400 |
| 2011/0131059 A1* | 6/2011 | Oscar | ............ | G06Q 10/10 705/3 |
| 2012/0239463 A1* | 9/2012 | Wertz | ............ | G06Q 10/06375 705/7.39 |
| 2012/0303382 A1* | 11/2012 | Paul | ............ | G06Q 10/10 705/2 |

OTHER PUBLICATIONS

EconPort, Claculating Inflation with Price indexes, 2006, 1 page.*
Brudon et al., Indicators for monitoring national drug policies, A practical manual, Second edition, World Health Organization, 1999, 8 pages.*
EconPort, Calculating Inflation with Price indexes, 2006, 1 page.*
Express Scripts 2009 Drug Trend Report, Apr. 2010, 25 pages.*
Design, data weighing and design effects in Dutch regional health surveys, SISA, 2006, 6 pages.*

* cited by examiner

METHODS AND SYSTEMS FOR DETERMINING DRUG TREND AND DRUG INFLATION

CROSS-REFERENCE TO A RELATED APPLICATION

This application claims the benefit of U.S. provisional patent application 61/622,506, filed on 10 Apr. 2012, entitled "Method and Systems for Determine Drug Trend and Drug Inflation," the entire disclosure of which is incorporated herein by reference.

FIELD

The field relates to prescription drug usage and cost, and more particularly to determination of usage trends and price inflation of prescription drugs.

BACKGROUND

Pharmacy benefit managers, as part of its services, typically provide prescription drug programs for clients that may, for example, sponsor drug benefit programs for members. As part of the providing the prescription drug programs for clients, pharmacy benefit managers may adjudicate claims from pharmacies for prescriptions obtained by members at the pharmacy. The PBM may also reimburse pharmacies for prescription obtained by members at the pharmacies. The PBM may also bill clients for the cost of prescriptions adjudicated by the pharmacy benefit manager.

DETAILED DESCRIPTION

Figure 1:
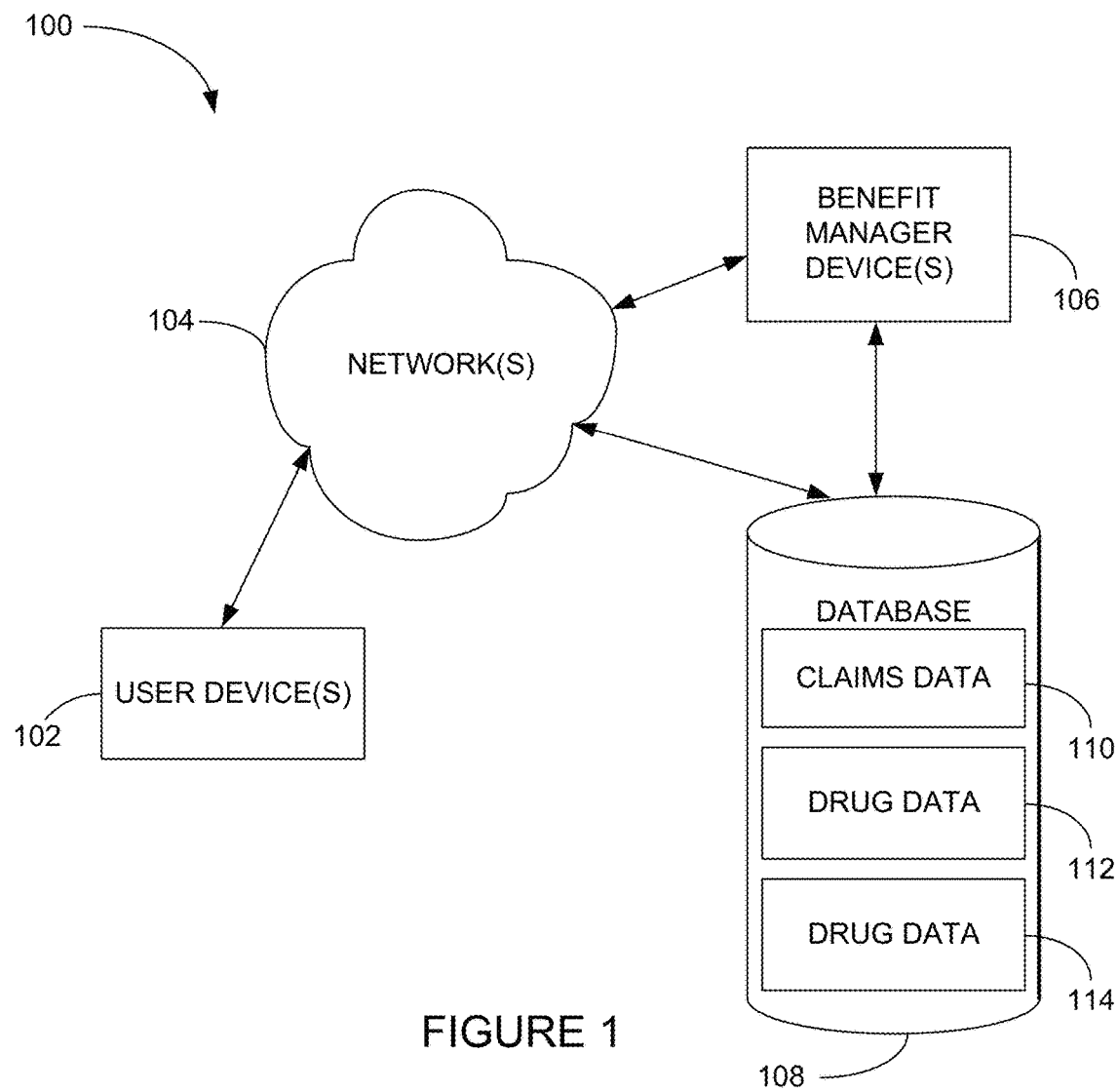
FIG. 1 is a block diagram of an example system, according to an example embodiment.

Example methods and systems for drug trend and drug inflation reporting are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a client engages a pharmacy benefit manager (PBM) to offer a drug benefit program to members. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. A person who is a participant or member of a drug benefit program offered by the client may obtain prescription drugs according to pricing, pharmacy selection, rebates, discounts and the like provided by the terms of the drug benefit program.

In some instances, the cost of sponsoring a drug benefit plan may be a relatively significant expenditure for a client of the PBM. It may, therefore, be useful for clients to be able to track expenses associated with sponsoring a drug benefit plan, and to be able to identify trends related to expenses and usage of sponsored drug benefit programs. For example, the ability to recognize trends relating to prescription drug usage and expenses associated with a drug benefit plan may allow a client of the PBM to make timely decisions regarding expected costs of funding a drug benefit plan. In some instances, the ability to recognize trends within prescription drug usage, prescription prices, and expenses associated with sponsoring a drug benefit plan may allow clients of the PBM to make decisions regarding drug benefit plan offerings and management.

In some instances, prescription drug trends may be an important factor in general healthcare and related financial guidance. For example, prescription drug trends may provide an indicator of future healthcare costs. Prescription medications may often be a first line of treatment for conditions and, as such, may provide an indication of future healthcare utilization for more expensive healthcare utilization such as hospital stays, medical procedures, and the like. For example, a person taking an oral diabetic medication might only require a few physician visits for medical claims early on in the progression of the disease. However, the person taking the oral diabetic medications may be predicted to have much more intensive medical needs in future years as their disease progresses.

One trend related to prescription drug usage and expenses associated with drug benefit plans may include the change of drug prices over time. Drug prices may change over time, for example, as a result of inflation, competitive changes in the marketplace that may result from the introduction of generic equivalent drugs, drug shortages, or new therapies. Drug price changes may be realized on an individual drug basis and/or with respect to groups of drugs that may have a common attribute or characteristic. For example, generic drugs, or brand drugs, as a group, may experience price changes over time. Similarly, drugs associated with certain therapies (e.g., drugs related to the treatment of diabetes) may experience an overall price change with time. The relative price change over time of generic drugs and/or of brand drugs may provide information that may be useful for planning expenses and/or structuring drug benefit plans. For example, a downward change in the price of generic drugs, and the degree of downward change, may allow a drug benefit plan sponsor and/or a PBM to design drug benefit plan incentive to motivate members to increase utilization of generic drugs. By knowing the magnitude of the downward change, the drug benefit plan sponsor and/or the PBM may be able to devote an appropriate level of expenditure of such incentives based on expended savings that may result from such incentives.

In some embodiments, a prescription drug price index may be developed that may enable changes in drug prices to be tracked overtime. The price index may, for example, track the change in price of one, or more than one, groups of drugs over time. The price index may, in some embodiments, be based on a relative utilization of drugs, such that drugs with a higher utilization may impart a greater influence on the price index than drugs with a lower utilization. In some embodiments, the price index may be relative to a baseline time period. In such an embodiment, the price index may indicate a change in price relative to a price of the drug, or drugs, during the baseline time period.

In some embodiments, trends may be determined within various prescription drug usage and pricing metrics. Metrics that may be tracked include, for example, expenditures related to sponsoring a drug benefit plan, expenditures for various therapy classes, utilization of drugs according to various therapy classes, brand name drug utilization, generic drug utilization, and the like. Trends may be determined by comparing changes in metrics relative to a baseline time period. For example, year-to-date metric values for a given year may be compared with year-to-date values for corresponding time periods in previous years. In some embodiments, metrics for a given month in a given year may be compared with metrics for a corresponding month in a previous year. Various other comparisons and/or comparison timeframes may be implemented for examining trends related to prescription drug usage and/or drug benefit plan usage and expenses.

FIG. 1 is a block diagram of an example system 100, according to an example embodiment. The system 100 is an example embodiment in which drug trends and drug inflation may be determined. The drug trends and/or drug inflation may be determined for a single drug, multiple drugs in a single class, multiple drugs in multiple classes, or the like. The system 100 includes a user device 102 in communication with a benefit manager device 106 over a network 104. The system may also include a database 108.

The user device 102 is used by a device operator. The device operator may be an employee or contractor of a benefit manager, a member of an organization that tracks drug trend and/or drug inflation, payers, consultants, healthcare and insurance actuaries, or the like. Other device operators that have been provided with credentials may also operate the user device 102. In some embodiments, the user device 102 may provide an output may in the form of an electronic or hardcopy report, a transmission in which an inflation rate and/or trend information is included, a user interface in which the output is displayed, a suggested aspect of a drug benefit based on the inflation rate and/or the trend information, a suggested modification of an existing drug benefit based on the inflation rate and/or trend information, or the like.

In some embodiments, the device operator has credentials to obtain drug trend and drug inflation information. In other embodiments, the device operator can readily access the drug trend and drug inflation information without the use of credentials.

The user device 102 may be a stand-alone device that solely provides at least some of the functionality to enable the determination of drug trends and drug inflation, or may be a multi-use device that has functionality outside of determining drug trends and drug inflation as described herein.

Examples of the user device 102 include a set-top box (STB), a receiver card, a mobile telephone, a personal digital assistant (PDA), a display device, a portable gaming unit, and a computing system; however other devices may also be used. For example, the user device 102 may include a mobile electronic device, such an IPHONE or IPAD device by Apple, Inc., mobile electronic devices powered by ANDROID by Google, Inc., and a BLACKBERRY device by Research In Motion Limited. The user device 102 may also include other computing devices, such as desktop computing devices, notebook computing devices, netbook computing devices, gaming devices, and the like. Other types of electronic devices may also be used.

The network 104 by which the user device 102 communicates with the benefit manager device 106, and/or the database 108 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for the management of a drug benefit program. While the entity operating the benefit manager device 106 is typically a PBM, other entities may operate the benefit manager device 106 either on behalf of themselves, the PBM, or another entity. In some embodiments, a PBM that provides the drug benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary to determine appropriate co-pay, coinsurance, and deductible for the prescription drug, and performing a DUR on the member. The PBM then provides a response to the pharmacy following performance of the aforementioned operations. As part of the adjudication, the client (or the PBM on behalf of the client) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher.

The user device 102 may be in a client-server relationship with the benefit manager device 106, a peer-to-peer relationship with the benefit manager device 106, and/or in a different type of relationship with the benefit manager device 106.

The benefit manager device 106 may be in communication directly (e.g., through local storage) and/or through the network 104 (e.g., in a cloud configuration or software as a service) with a database 108. The database 108 may be deployed on the user device 102, the benefit manager device 106, both the user device 102 and the benefit manager device 106, partially on the user device 102 and partially on the benefit manager device 106, on a separate device, or may otherwise be deployed. The database 108 may store claims data 110, drug data 112, and/or prescription data 114.

The claims data 110 includes information regarding pharmacy claims adjudicated by the PBM under a drug benefit program provided by the PBM for one, or more than one, clients. In general, the claims data 110 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

The drug data 112 may include drug name (e.g., technical name and/or common name), other names by which the drug is known by, active ingredients, an image of the drug (e.g., in pill form), and the like. The drug data 112 may include information associated with a single medication or multiple medications.

The prescription data 114 may include information regarding prescriptions that may be issued by prescribers on behalf of patients, who may be members of the drug benefit plan, for example to be filled by a pharmacy. Examples of the prescription data 114 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.)

Certain data from the database 108 may be stored on the user device 102 and/or on the benefit manager device 106 separate from or in addition to the data stored in the database 108. In some embodiments, the data may be stored on the user device 102 and/or on the benefit manager device 106 instead of in the database 108.

While the system 100 in FIG. 1 is shown to include single devices 102, 106, multiple devices may be used. The devices 102, 106 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106 or in parallel to link the devices 102, 106.

Figure 2:
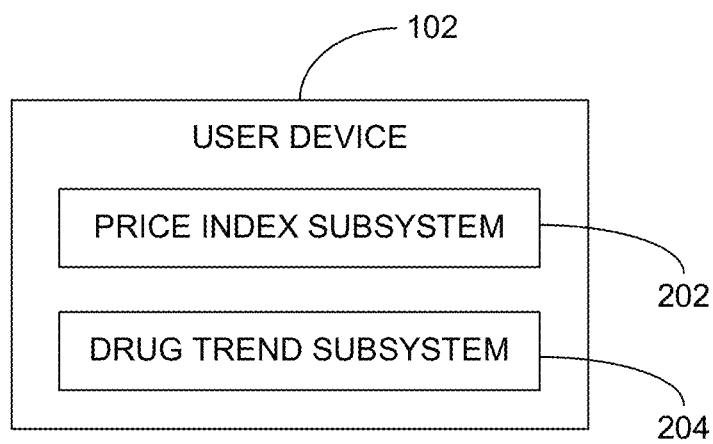
FIG. 2 is a block diagram of an example user device that may be deployed within the system of FIG. 1, according to an example embodiment.

FIG. 2 illustrates the user device 102, according to an example embodiment. The user device 102 may be used by a device operator to determine drug trends and/or drug price inflation. The user device 102 may be deployed in the system 100, or may otherwise be used.

The user device 102 may include a price index subsystem 202 and a drug trend subsystem 204. The price index subsystem 202 may generally enable price changes for prescription drugs to be tracked over time. The drug trend subsystem 204 may enable determination and tracking of various metrics relating to prescription drug usage, drug benefit plan attributes, and/or prescription drug costs.

Figure 3:
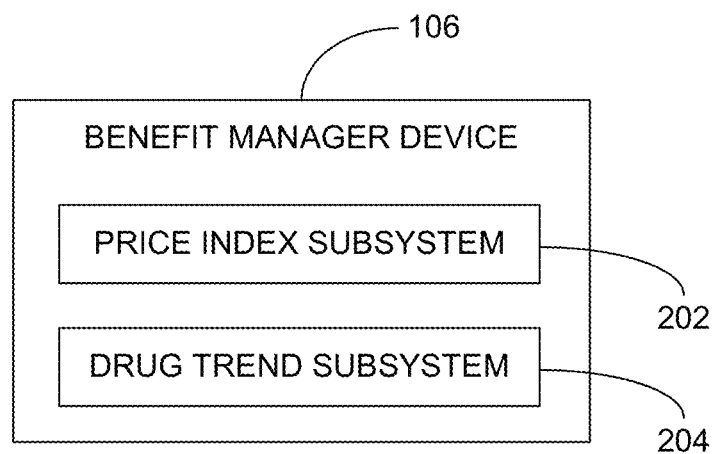
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may be deployed in the system 100, or may otherwise be used.

The benefit manager device 106 may include the price index subsystem 202 and drug trend subsystem 204. In some embodiments, the price index subsystem 202 and/or the drug trend subsystem 204 when used may provide server-side functionality to the user device 102. By way of example, the price index subsystem 202 and/or the drug trend subsystem 204 may be at least partially deployed in both the user device 102 and the benefit manager device 106. The user device 102 may then perform some of the functionality while other functionality is performed by the benefit manager device 106.

Figure 4:
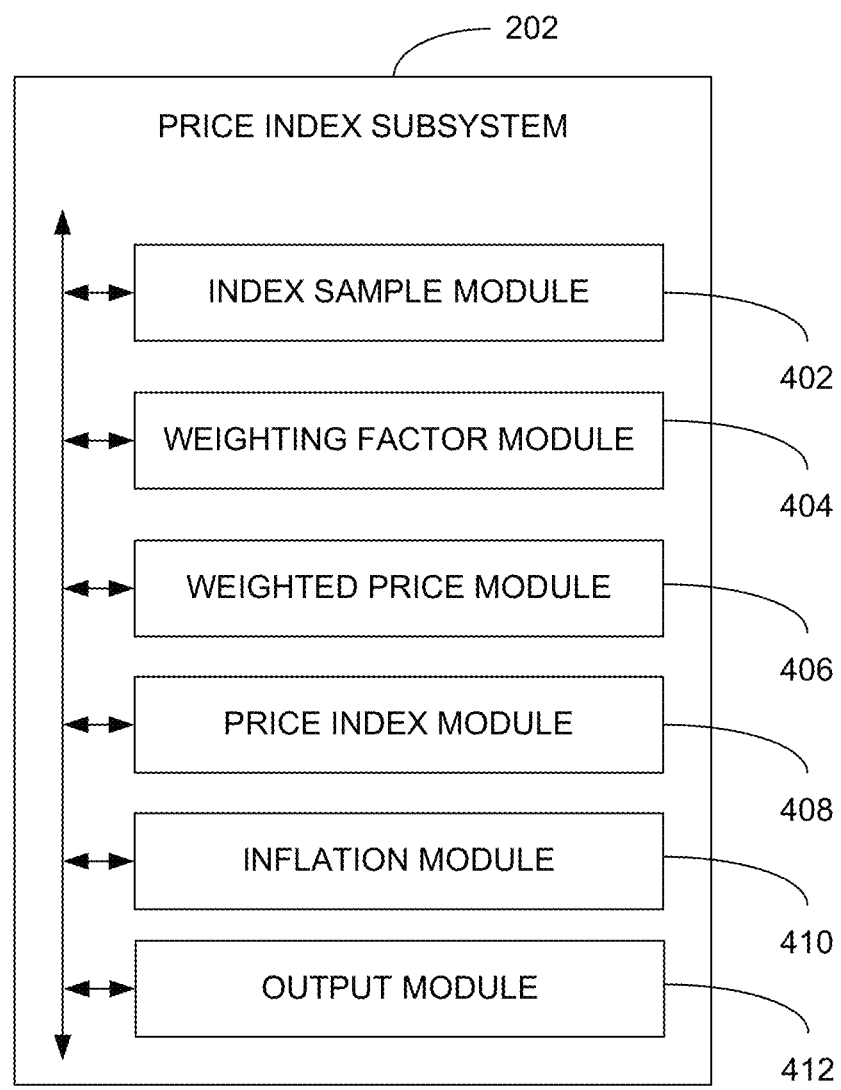
FIG. 4 is a block diagram of an example price index subsystem that may be deployed within the user device of FIG. 2 or the benefit manager device of FIG. 3, according to an example embodiment.

FIG. 4 illustrates an example price index subsystem 202 that may be deployed in the user device 102, the benefit manager device 106, or otherwise deployed in another system. One or more modules are communicatively coupled and included in the price index subsystem 202 to enable a price change in prescription drugs, such as an inflation cost, to be determined. The modules of the price index subsystem 202 that may be included are an index sample module 402, weighting factor module 404, a weighted price module 406, a price index module 408, an inflation module 410, and an output module 412.

In some embodiments, the modules of the price index subsystem 202 may be distributed so that some of the modules are deployed in the user device 102 and some modules are deployed in the benefit manager device 106. In one embodiment, the modules are deployed in memory and executed by a processor coupled to the memory. The functionality contained within the modules 402-412 may be combined into a lesser number of modules, further divided among a greater number of modules, or redistributed among existing modules. Other configurations including the functionality of the modules 402-412 may be used.

In some embodiments, the index sample module 402 may select an index sample including an identification of multiple drugs. In general, the index sample may include the prescription drugs for which the price index may be determined. The price index may generally allow the change in the price of the prescription drugs to be tracked over time, e.g., which may indicate inflationary price changes of the prescription drugs, prices changes based on competitive changes in the marketplace (e.g., resulting from competition from equivalent drugs and/or new therapies, etc.), and the like. The index sample may include various different categories and/or groups of prescription drugs. For example, the index sample may include all prescription drugs, prescription drugs within a defined class of drugs (e.g., brand name drugs, generic drugs, or the like), prescription drugs within a defined therapy class, or the like. In some embodiments, a price index may be determined for multiple different categories or classes of prescription drugs.

In an illustrative example, a price index may be determined for generic prescription drugs. In such an embodiment, the index sample module 402 may select an index sample including an identification of generic prescription drugs. Selecting the index sample may include, for example, accessing the claims data 110 and/or the drug data 112 associated with the generic drugs of the index sample. For example, in an embodiment, the index sample module 402 may query the database 108 relative to the claims data 110 for generic prescription drugs for which pharmacy claims were adjudicated. In some embodiments, the claims data 110 may include an indicator that a prescription filled by a pharmacy is a generic drug. In some embodiments, the index sample module 402 may further query the drug data 112, which may include an indication that a prescription drug is a generic prescription drug. In such an embodiment, the index sample module 402 may query the claims data 110 relative to drugs for which prescriptions were filled, and may filter the query results based on information included within the drug data 112 to identify which drugs within the query results include generic drugs. An index sample for other groups of drugs, (e.g., brand name drugs, drugs associated with a defined therapy class, etc.) may be similarly selected.

In an embodiment, the index sample module 402 may select the index sample including based on a drug utilization associated with each of the drugs. For example, in some instances a drug, and/or more than one drug, may be infrequently used, but may be very expensive, and therefore may have a large impact on any pricing metric. According to an embodiment, the effect of such outliers may be reduced and/or eliminated by selecting the index sample to include the most utilized prescription drugs. In an embodiment, utilization may be calculated for each drug within the sample index. In such an embodiment, the most utilized drugs may be selected for the index sample.

In some instances several drugs including the same active ingredient, route of administration, and dosage may be distributed under different drug names. In an embodiment, more than one drug including the same active ingredient, route of administration, and dosage may be considered a single drug for the purpose of determining utilization. In an embodiment, the drug data 112 may include a Generic Product Identifier (GPI-14), e.g., which may include an identification of multiple drugs as being equivalents with respect to active ingredient, route of administration, and dosage. Accordingly, in some embodiments the index sample module 402 may determine an aggregate utilization for drugs having a common GPI-14 indicator.

In some embodiments, the index sample module 402 may determine the utilization of the prescription drugs for a common time period. In an embodiment, the common time period may be a baseline, e.g., against which changes in price of the prescription drugs may be measured. Various suitable time periods may be implemented. For example, the index sample module 402 may determine the utilization of the drugs for the same one-month time period. In such an embodiment, the one-month time period may be a baseline time period. Time periods other than one month may also be utilized. For example, in some embodiments, the time period may be a three-month time period, a six-month time period, a one-year time period, or any other time period. The utilization of the prescription drugs may be based on pharmacy claims adjudicated for the drugs during the baseline time period. In an embodiment, determining the utilization of the prescription drugs may include accessing the claims data 110, e.g., to determine the number of prescriptions, quantity of medication, and dosage for prescriptions adjudicated for the prescription drugs.

In an embodiment, determining utilization of the drugs may include determining a normalized prescription. For example, various different drugs may be used by a member for different amounts of time (e.g., a prescription for an acute condition with a prescribed ten-day course of treatment, a prescription for a maintenance medication requiring ongoing treatment), and/or prescriptions may be filled having different supplies (e.g., a prescription fill including a thirty-day supply, or a prescription fill including a ninety-day supply). In an embodiment, a normalized prescription may be calculated as a number of thirty-day prescriptions. For example, a prescription including a ten-day supply of the prescription drug may be considered a 0.3 thirty-day prescription, and a prescription including a ninety day supply may be considered 3 thirty-day prescriptions for the purpose of determining utilization.

In some embodiments, the utilization of a drug (or group of drugs having a common GPI-14 indicator) may be determined as the number of normalized prescriptions (e.g., the number of thirty day prescriptions) for the baseline time period divided by the total number of normalized prescriptions for all of the drugs included in the index sample (e.g., for all generic prescription drugs, in the foregoing example) during the baseline time period.

In an embodiment, the index sample module 402 may select the prescription drugs with the highest utilization during the baseline time period for inclusion in the sample index. In an embodiment, the index sample module 402 may select the prescription drugs having the highest utilization that account for a threshold utilization percentage. For example, for a threshold utilization of eighty percent, the prescription drugs having the highest utilization which cumulatively account for eighty percent of the total utilization may be selected for inclusion in the index sample. As such, in an embodiment, the prescription drugs in the aggregate accounting for the lowest twenty percent of drug utilization (e.g., the least utilized prescription drugs) may be excluded from the index sample. Threshold utilizations other than eighty percent may be utilized. For example, any threshold utilizations greater than fifty percent may be utilized, thereby including in the index sample the drugs that account for the majority of the total utilization of the plurality of prescription drugs. For example, other percentages such as 70%, 75%, 85%, 90%, 95%, 99%, or the like may be used.

In some embodiments, the weighting factor module 404 may calculate a weighting factor associated with each of the drugs included in the index sample. The weighting factor associated with each of the prescription drugs may be based on a relative utilization for each of the drugs. In an embodiment, the weighting factor may be calculated based on a number of normalized prescriptions for each of the drugs during the baseline time period relative to the sum of the number of normalized prescriptions for all of the drugs included in the index sample during the baseline time period. The normalized prescriptions may be, for example, the number of thirty-day prescriptions for the drug. For example, a ten day prescription for a prescription drug may be 0.3 thirty-day prescriptions. In a similar manner 90 ten-day prescriptions for the prescription drug may be 30 thirty-day prescriptions.

In an example embodiment, the weighting factor may be calculated as:

$$w_i = \frac{RX_i}{\sum_i^N RX_i}$$

wherein $w_i$ is the weighting factor drug i, $RX_i$ is the total number of normalized (e.g., thirty-day) prescriptions for drug i during the baseline time period, and $\Sigma_i^N RX_i$ is the sum of normalized prescriptions across the N drugs that constitute the index sample.

In some embodiments, the weighted price module 406 may calculate a first weighted price of for each of the drugs for a first time period. The first time period may include the baseline time period. In an embodiment, the first weighted price for the drugs for the first time period may be based on the weighting factor associated with each of the drugs and a cost associated with each of the drugs for the first time period. In such an embodiment, the first weighted price for the drugs may be calculated using the weighting factor associated with each of the drugs (e.g., which may be based on a utilization of the drug during the baseline time period). For example, the weighted price may be calculated as the sum of the weighting factor associated with each drug multiplied by the drug cost associated with the respective drug for a normalized prescription (e.g., for a thirty-day prescription) of the drug, for each of the drugs in the index sample.

In an embodiment, the drug cost for a normalized prescription (e.g., a thirty-day prescription) of the drug may be calculated as the drug cost divided by the number of days of the prescription multiplied by thirty. For example, a prescription fill for a ten-day supply of a drug having a drug cost of $10 may have a daily drug cost of $1 and a normalized thirty-day prescription cost of $30. In some embodiments, the drug cost for the purpose of calculating the weighted price may include the drug cost minus any rebates to be paid to the PBM by the drug suppliers. In some embodiments, the rebate may be estimated based on a global rebate from a period prior to the baseline period. For example, a total rebate received by the PBM may be apportioned to individual drugs included within the index sample based on a utilization proportion of each drug in the index sample.

In an example embodiment, the first weighted price (e.g., the weighted price for the baseline time period) for a thirty-day normalized prescription may be calculated as:

$$P_{base\ m, Rxs30} = \sum_{i=1}^{N} w_i * C_{i, base\ m, Rxs30}$$

wherein $P_{base m,\ Rxs30}$ is the weighted price for the drugs included in the index sample, $w_i$ is the weighting factor associated with the drug i, $C_{i,\ base\ m,\ Rxs30}$ is the price per thirty-day normalized prescription for the drug i in the baseline time period.

In some embodiments, the weighted price module 406 may also calculate a second weighted price for the drugs for a second time period. In a similar manner as the first weighted price, the second weighted price for the drugs for the second time period may be based on the weighting factor associated with each of the drugs and a cost associated with each of the drugs for the second time period. The drugs for which the second weighted price is calculated may include the drugs included within the sample index. The weighting factor may include the weighting factor determined based on utilization of each of the drugs included within the baseline time period. As such, the second weighted price may be calculated for the same drugs and using the same weighting factor as utilized for calculating the first weighted price. As such, in some embodiments, for the purpose of calculating the second weighted price the utilization may be held fixed at the same level as utilized for calculating the first weighted price.

In an embodiment, the second time period may include a time period for which the price of the plurality of drugs may be compared to the price of the drugs during the baseline time period. As such, the cost of the drugs included within the index sample at the second time period may be compared to the cost of the drugs included within the index sample at the first time period (e.g., the baseline time period).

For example, the weighted price may be calculated as the sum of the product of each weighting factor associated with each drug and the drug cost associated with the respective drug for a normalized prescription (e.g., for a thirty-day prescription) of the drug, for each of the drugs in the index sample. In some embodiments, the drug cost for the purpose of calculating the weighted price may include the drug cost minus any rebates to be paid to the PBM by the drug suppliers. In an embodiment, the rebate may include the estimated rebate utilized in calculating the first weighted price.

In an example embodiment, the second weighted price (e.g., the weighted price for the second time period) for a thirty-day normalized prescription may be calculated as:

$$P_{Month\ m, Rxs30} = \sum_{i=1}^{N} w_i * C_{i, Month\ m, Rxs30}$$

wherein $P_{Month\ m,\ Rxs30}$ is the weighted price for the drugs included in the index sample in the second time period, $w_i$ is the weighting factor associated with the drug i, $C_{i,\ base\ m,\ Rxs30}$ is the price per thirty-day normalized prescription for the drug i in the baseline time period.

In some embodiments, the price index module 408 may calculate a price index for the second time period based on the first weighted price and the second weighted price. In an embodiment, the index may be calculated based on a ratio of the second weighted price to the first weighted price. In some embodiments, the ratio of the second weighted price to the first weighted price may be multiplied by a scaling factor, e.g., to provide an index value in a desired general numerical range.

In an example embodiment, the price index for a thirty-day normalized prescription may be calculated as:

$$\text{ESI\_Index}_{Month\ m, Rxs30, Generic} = \frac{P_{Month\ m, Rxs30, Generic}}{P_{base\ m, Rxs30, Generic}} \times 100$$

wherein $\text{ESI\_Index}_{Month\ m, Rxs30, Generic}$ is a price index for a thirty-day normalized prescription for generic drugs for month m relative to a base month.

In some embodiments, the inflation module 410 may calculate an inflation rate based on a rate of change of the price index. In an embodiment, the inflation rate may include a percent change in the price index between two different time periods (e.g., between the baseline time period and the second time period, between the second time period and another time period, etc.).

In some embodiments, the index sample may be periodically updated, e.g., to account for possible changes in consumer behavior, changes in drugs on the market, changes in drug status (e.g., introduction of generic equivalents to brand drugs), and the like. In such an embodiment, the sample index may be re-selected in a generally similar manner as discussed, utilizing drug utilization associated with a new baseline time period. Similarly, the weighting factor and baseline price may be recalculated to reflect any changes in utilization of drugs.

In an embodiment, the price index may allow the real cost of inflation and/or changes in price of prescription drugs to be tracked. Additionally, in an embodiment in which the index sample, weighting factor, and/or baseline weighted price may be periodically updated, changes in consumer preferences, changes in competitive factors (e.g., new drugs entering the market, drugs leaving the market because of recalls, etc.) may be taken into account.

In an embodiment, the output module 412 may generate an output based on the inflation rate and/or the price index itself. The output may be in the form of an electronic or hardcopy report, a transmission in which the inflation rate is included, a user interface in which the output is displayed, a suggested aspect of a drug benefit based on the inflation rate, a suggested modification of an existing drug benefit based on the inflation rate, or the like.

In some embodiments, the output module 412 may directly, or in communicate with other modules and/or devices, utilize the inflation rate and/or price index. For example, a financial system or module may utilize the inflation rate and/or price index to project future utilization, growth, inflation/deflation, or the like. A plan design system or module may utilize the inflation rate and/or price index with the designing of benefit plans. For example, the plan design system or module may provide different plan options, different plan configurations, suggested plan modifications, or the like based on the inflation rate and/or price index. The inflation rate and/or price index may otherwise be used directly or indirectly by the benefit manager, a plan sponsor, or a different party.

Figure 5:
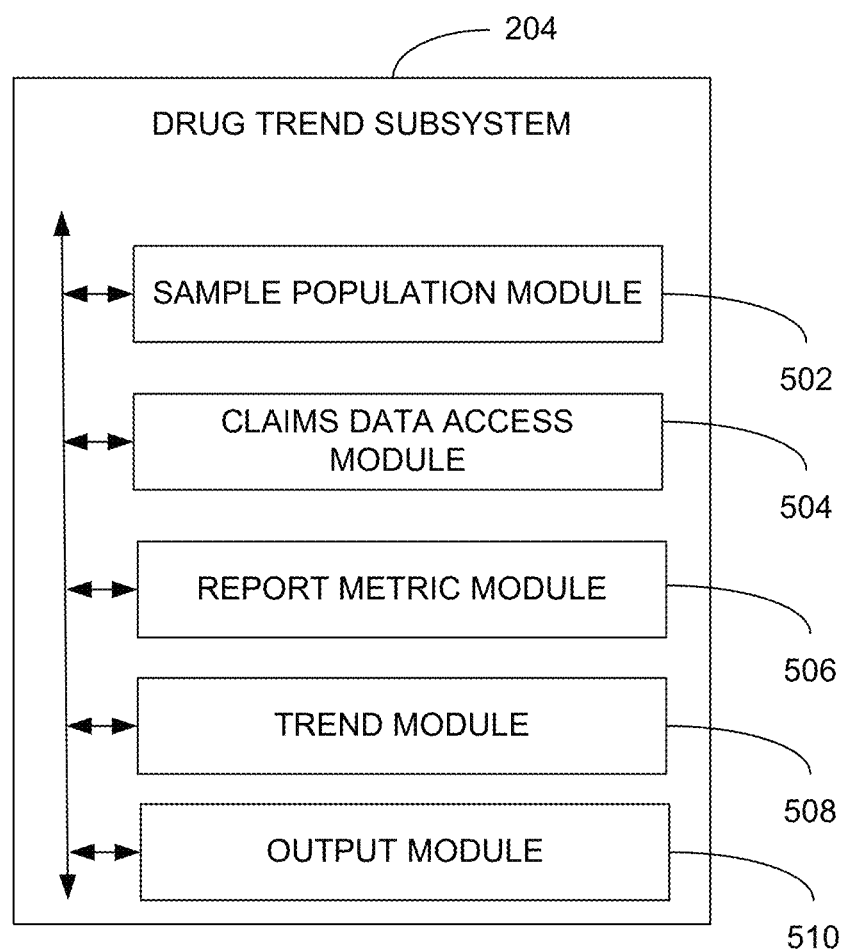
FIG. 5 is a block diagram of an example drug trend subsystem that may be deployed within the user device of FIG. 2 or the benefit manager device of FIG. 3, according to an example embodiment.

FIG. 5 illustrates an example the drug trend subsystem 202 that may be deployed in the user device 102, the benefit manager device 106, or otherwise deployed in another system. One or more modules are communicatively coupled and included in the drug trend subsystem 202 to enable trends associated with various drug usage and pricing metrics to be determined. The modules of the drug trend subsystem 202 that may be included are a sample population module 502, a claims data access module 504, a report metric module 506, a trend module 508, and an output module 510.

In some embodiments, the modules of the drug trend subsystem 202 may be distributed so that some of the modules are deployed in the user device 102 and some modules are deployed in the benefit manager device 106. In one embodiment, the modules are deployed in memory and executed by a processor coupled to the memory. The functionality contained within the modules 502-510 may be combined into a lesser number of modules, further divided among a greater number of modules, or redistributed among existing modules. Other configurations including the functionality of the modules 502-510 may be used.

A trend sample population may be selected by the sample population module 502. The sample population may include members of a drug benefit plan. For example, the sample population of the members may include members of a single drug benefit plan, or may include members of more than one drug benefit plan. In an embodiment, a trend may be determined relative to a first time period (e.g., a baseline time period) and a second time period (e.g., a time period for which the trend relative to the baseline timer period may be determined). In an embodiment, the trend sample population may include members of the one or more drug benefit plans that were members of the one or more drug benefit plans for both the first time period and the second time period.

In an embodiment, the claims data access module 504 may access pharmacy claims data associated with each of the members included within the trend sample population. For example, the claims data access module 504 may access the claims data 110 stored within the database 108. The claims data 110 may include, for example, an indication of prescriptions adjudicated on behalf of each of the members during the first time period and the second time period. The prescription adjudication data included in the claims data 110 on behalf of each of the members may include, for example, an indication of how many prescriptions were filled for each member, what drug each prescription included, the supply duration of medication included in each filled prescription, a cost of the drug, and the like. In some instances, the claims data access module 504 may access the drug data 112 stored within the database 108, e.g., to ascertain information about one, or more than one, drugs identified in one, or more than one, prescriptions. For example, such information may include a cost of a drug, rebate information associated with a drug, a brand name/generic status of the drug, or the like.

The report metric module 506 may calculate a report metric for a first time period based on the pharmacy claims data 110. For example, in an embodiment, the report metric may include a drug utilization associated with the members. The drug utilization may be based on, for example, the number of prescriptions filled by the members. In one embodiment, utilization may be based on the number of prescriptions per member included within the trend sample population.

In an embodiment, the drug trend may be based on a number of normalized prescriptions on an annualized basis. For example, the number of prescriptions filled by the members may be calculated by converting the pharmacy claims data 110 associated with the members and/or the prescription data 114 associated with the members into normalized prescription data. Normalized prescription data may include, for example, data based on a thirty-day prescription bases. For example, a prescription including a ten day supply of medication may be converted to a 0.3 thirty-day prescription. Similarly, a ninety day prescription may be converted to 3 thirty-day prescriptions. In an embodiment, the drug utilization may be calculated based on a per-member-per year basis. In such an embodiment, the utilization may be calculated as the number of normalized prescriptions (e.g., number of thirty-day prescriptions) per member years. In an example embodiment, the number cumulative number of normalized thirty-day prescriptions for all members included within the trend sample population may be divided by the number of member years represented by the first time period to provide a per-member-per-year utilization metric. For example, for a trend sample population including 1000 members, and a first time period of one month, the number of member years may be equal to the number of members (e.g., 1000 in the example embodiment) multiplied by the months included in the first time period (e.g., one month in the example embodiment), and dividing the product by 12 (e.g., the number of months in a year). In the example embodiment, including 1000 members and a one-month first time period, the first time period would represent 83.3 member years.

In an embodiment, the report metric module 506 may calculate drug utilization on a therapy class basis. In such an example, the utilization may be calculated only relative to drugs associated with a defined therapy class (e.g., drugs associated with diabetes treatment, drugs associated with high blood cholesterol treatment, or the like). According to various embodiments, a report metric based on utilization on a therapy class basis may be calculated as a number of prescriptions divided by a total number of members included within the trend sample population, a number of normalized prescriptions per member year (e.g., a per-member-per-year basis), and/or another suitable indicator.

In an embodiment, the report metric may include a prescription cost metric. For example, the report metric module 506 may calculate a total cost for all prescriptions for the trend sample population for the first time period. In such an embodiment, a cumulative cost associated with each prescription for all members of the trend sample population may be calculated. In an embodiment, the report metric may be based on a total cost, on a per-member-per-year basis, or other suitable basis. In an example of a per-member-per-year basis, the cumulative cost for prescription drugs may be divided by the number of member years to provide the cost on a per-member-per-year cost. In an embodiment, the prescription cost metric may be based prescriptions associated with one, or more than one, therapy class.

In an embodiment, the report metric module 506 may calculate the report metric for the second time period based on the pharmacy claims data 110 for the second time period. The various report metrics discussed above may be calculated in a similar manner, utilizing claims data and/or drug data associated with the second time period.

In an embodiment, the first time period may include a time period within a first year and the second time period may include a corresponding time period within a second year. For example, the first time period may include a specific month (e.g., January) within a first year (e.g., 2011), and the second time period may include a corresponding month (e.g., January) in a subsequent year (e.g., 2012). According to such an embodiment, the first report metric and the second report metric may indicate utilization, cost, etc. for corresponding time periods in different years. In some embodiments, the first time period and the second time period may include any suitable time period. For example, the first time period may include a cumulative time period (e.g., a year-to-date time period) of the first year, and the second time period may include a corresponding cumulative time period in the subsequent year. As such, a difference in the report metric between the two time periods may indicate a change in the calculated metric (e.g., a change in utilization by members, a change in cost for sponsoring a drug benefit plan, or the like). In some embodiments, a difference across more than one report metric may provide an indication of a reason for a change in at least one of the more than one report metrics. For example, and increase in cost for the drug benefit plan between the two time periods may be, at least in part, explained by an increase in utilization between the two time periods.

In an embodiment, the trend module 508 may calculate a trend rate based on the report metric for the first time period and the report metric for the second time period. For example, the trend rate may include a percent change in the report metric for the second time period relative to the report metric for the first time period (e.g., which may include a baseline time period).

In an embodiment, the output module 510 may generate an output based on the trend rate. The output may be in the form of an electronic or hardcopy report, a transmission in which the trend rate is included, a user interface in which the output is displayed, a suggested aspect of a drug benefit based on the trend rate, a suggested modification of an existing drug benefit based on the trend rate, or the like. The output module 510 may be utilized otherwise as describe above with respect to the output module 412. In some embodiments, the functionality of the output modules 412, 510 may be combined together to generate a combined output.

Figure 6:
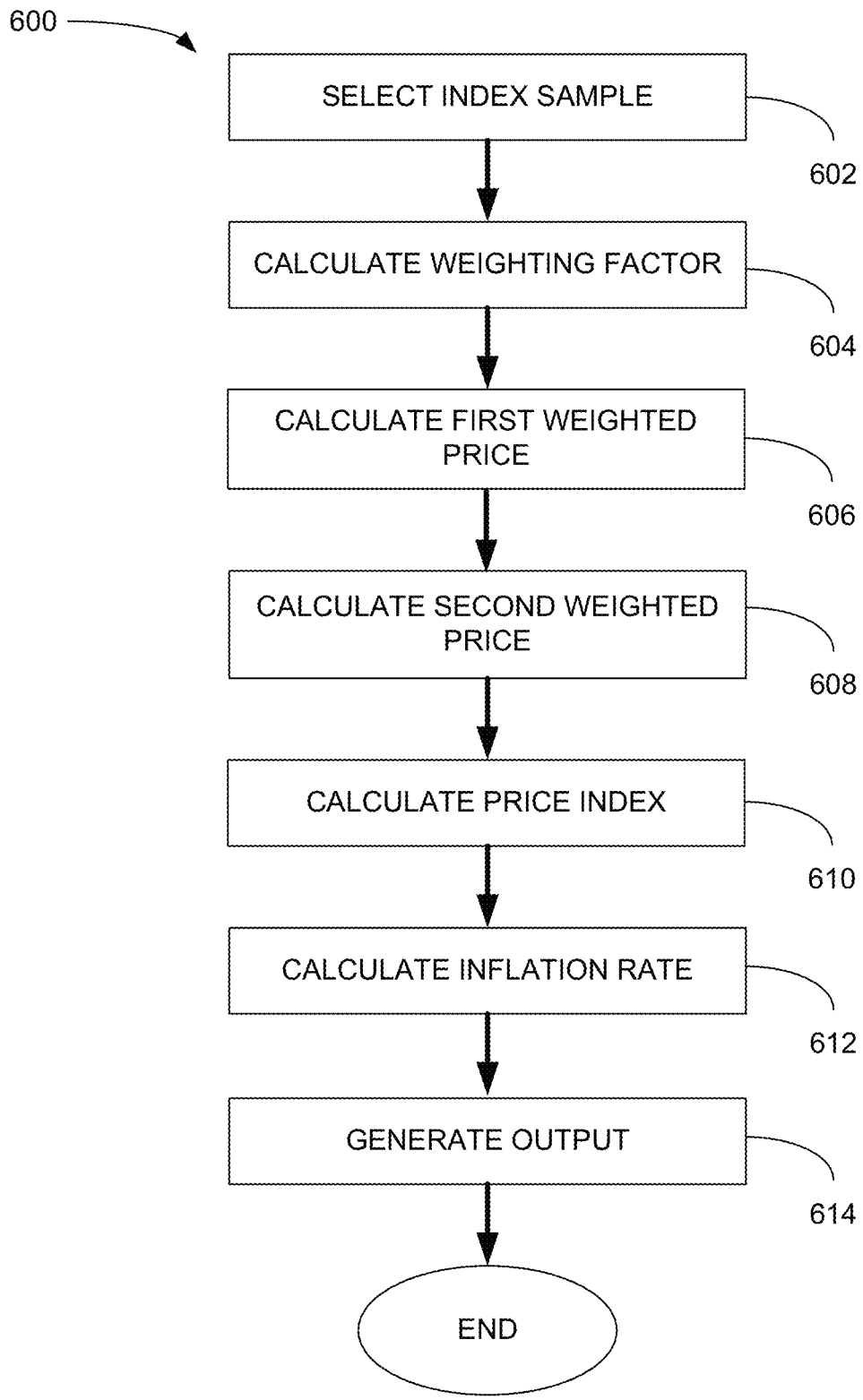
FIG. 6 is a process flow illustrating a method for drug price index determination, according to an example embodiment.

FIG. 6 illustrates a method 600 for determining a pricing index for prescription drugs, according to an example embodiment. The method 600 may be performed by the user device 102, by the benefit manager device 106, partially by the user device 102 and partially be the benefit manager device 106, or may be otherwise performed.

An index sample may be selected at block 602. The index sample may include prescription drugs. A change in the price of the drugs, as a group, may be determined based on the determined price index. In some embodiments, the index sample may be selected based on utilization of drugs during a first time period (e.g., a baseline time period against which subsequent prices may be compared). As such, in some embodiments, the price index may be based on the most utilized drugs in a group to which the price index may apply.

A weighting factor may be calculated at block 604 for the drugs included within the index sample. The weighting factor may be calculated for each of the drugs included within the index sample or a subset of the drugs. The weighting factor may be generally based on a relative utilization of each individual drug included within the index sample relative to the total utilization of all of the drugs included within the index sample.

A first weighted price may be calculated at block 606. The first weighted price may include a weighted price for the drugs included within the index sample for the first time period (e.g., the baseline time period). The first weighted price may generally be based on the cumulative value of each weighting factor multiplied by a drug cost for the respective drug during the first time period for all of the drugs included within the index sample. The drug cost may include the cost of the drug minus an associated estimated rebate for the drug. The estimated rebate for the drug may be based on an apportioned rebate received for the drug during a prior time period.

A second weighted price may be calculated at block 608. The second weighted price may include a weighted price for the drugs included within the index sample for a second time period. The second weighted price may generally be based on the cumulative value for each weighting factor multiplied by a drug cost for the respective drug during the second time period for all of the drugs included within the index sample. The drug cost may include the cost of the drug minus the associated estimated rebate for the drug.

A price index may be calculated at block 610. Calculating the price index may include calculating a ratio of the second weighted price to the first weighted price. In some embodiments, the ratio of the second weighted price and the first weighted price may be multiplied by a scaling factor, e.g., to place the price index in a desired numerical range.

An inflation rate may be calculated at block 612. The inflation rate may include the percent change between a first price index and a second price index. For example, the first price index may generally include the ratio of the second weighted price to the baseline weighted price. A second price index may generally include the ratio of a third weighted price (e.g., a weighted price at a third time period) to the baseline weighted price. Accordingly, the inflation rate may indicate a percent change in the price of the drugs in the index sample between the second time period and the third time period, for example.

An output may be generated at block 614 based on the inflation rate. The output may be in the form of an electronic or hardcopy report, a transmission in which the inflation rate is included, a user interface in which the output is displayed, a suggested aspect of a drug benefit based on the inflation rate, a suggested modification of an existing drug benefit based on the inflation rate, or the like.

Figure 7:
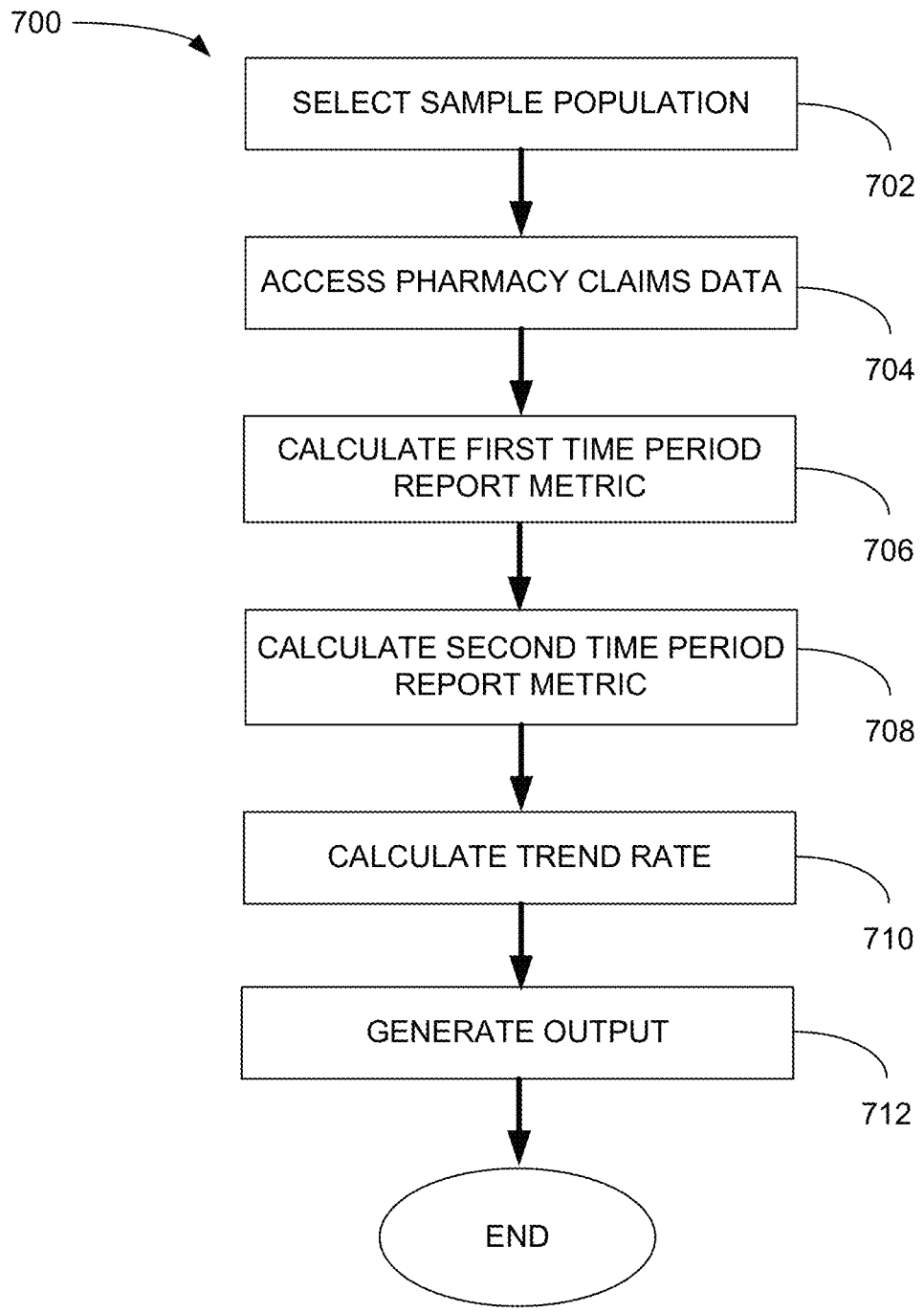
FIG. 7 is a process flow illustrating a method for drug trend determination.

FIG. 7 illustrates a method 700 for determining and tracking various metrics relating to prescription drug usage, drug benefit plan attributes, and/or prescription drug costs, according to an example embodiment. The method 700 may be performed by the user device 102, by the benefit manager device 106, partially by the user device 102 and partially be the benefit manager device 106, or may be otherwise performed.

In an embodiment, a trend sample population of members of one, or more than one, drug benefit plan may be selected at block 702. In an embodiment in which a trend may be determined relative to a first time period and a second time period, the trend sample population may include members of the one, or more than one, drug benefit plane who were enrolled in the drug benefit plan during both the first time period and the second time period.

Pharmacy claims data 110 may be accessed at block 704. The pharmacy claims data 110 may include pharmacy claims data associated with the members included within the trend sample population. The pharmacy claims data 110 may include an indication of prescriptions adjudicated on behalf of the members included within the trend sample population during the first time period and the second time period. In some embodiments, the pharmacy claims data 110 may include an indication of the prescription drugs prescribed to each member, a fill duration of the prescriptions, a cost of the drugs associated with the prescriptions, and the like.

A report metric for the first time period may be calculated at block 706. The report metric may include, for example, a utilization rate for all prescriptions during the first time period, a utilization rate for prescriptions associated with a defined therapy class during the first time period, a cost for prescriptions during the first time period, or the like. In some embodiments, the report metric may be based on a per-member-per-year basis. In some embodiments, the report metric may be based on a normalized prescription (e.g., a thirty-day prescription basis)

A report metric for the second time period may be calculated at block 708. The report metric may include, for example, a utilization rate for all prescriptions during the second time period, a utilization rate for prescriptions associated with a defined therapy class during the second time period, a cost for prescriptions during the second time period, or the like. In some embodiments, the report metric may be based on a per-member-per-year basis. In some embodiments, the report metric may be based on a normalized prescription (e.g., a thirty-day prescription basis)

A trend rate may be calculated at block 710. The trend rate may be based on, for example, a percent change in the report metric from the first timer period to the second time period.

An output may be generated at block 712 based on the trend rate. The output may be in the form of an electronic or hardcopy report, a transmission in which the trend rate is included, a user interface in which the output is displayed, a suggested aspect of a drug benefit based on the trend rate, a suggested modification of an existing drug benefit based on the trend rate, or the like.

Figure 8:
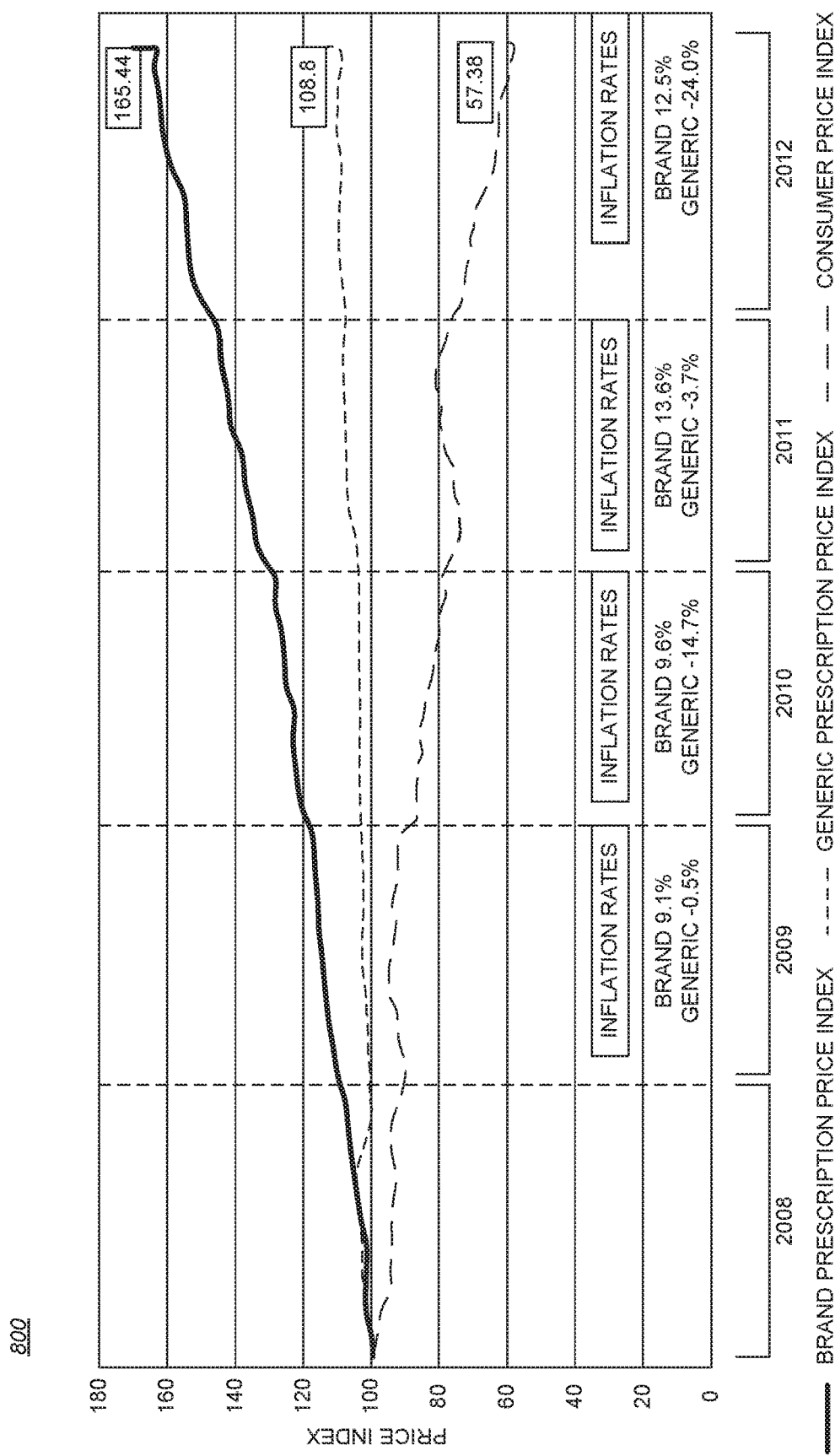
FIG. 8 is a an example display, according to an example embodiment.

FIG. 8 illustrates an example display 800 in accordance with an example embodiment. The display 800 may be generated and/or displayed on the user device 102, on the benefit manager device 106, or otherwise. The display 800 is an example of a prescription drug price index for a time period. However, other types of prices indexes for prescription drugs (or other items) may be generated and displayed.

The display 800 includes a horizontal x axis including a date range and a vertical y axis including a price index. The display shows three plots during the identified time period of 2008 through 2012. The first plot, a brand prescription price index, reflects a change from 100 to 165.44 through this time period. The second plot, a generic prescription price index, reflects a change from 100 to 57.38 through this time period. The third plot, a consumer price index, reflects a change from 100 to 108.8 through this time period. In general, the consumer price index reflects consumer inflation. As such, an item that cost one hundred dollars at the beginning of 2008 would cost one hundred eight dollars and eighty cents at the end of 2012. The changes in values shown in the display 800 reflect, among other things, that during the time periods the cost for brand name prescription drugs has risen while the cost for generic prescription drugs has fallen.

In addition, the display 800 identifies inflation rates during the various time periods. The reflected inflation rates for brand prescription drugs during 2009 was 9.1%, while the reflected inflation rates for generic prescription drugs was −0.5%. The reflected inflation rates for brand prescription drugs during 2010 was 9.6%, while the reflected inflation rates for generic prescription drugs was −14.7%. The reflected inflation rates for brand prescription drugs during 2011 was 13.6%, while the reflected inflation rates for generic prescription drugs was −3.7%. The reflected inflation rates for brand prescription drugs during 2012 was 12.5%, while the reflected inflation rates for generic prescription drugs was −24.7%.

In some embodiments, various insights may be obtained from the display 800. The insights may include one or more of the following:

Brand drug prices increased much faster than the overall inflation rate from December 2011 to December 2012, while generic prices plummeted. This pattern reflects the impact of the patent cliff—the wave of patent expirations for blockbuster drugs—and underscores the unprecedented opportunity to move patients to generic drugs when possible.

Brand inflation and generic deflation continue unabated. While the cost (in 2008 dollars) for an unchanged market basket of brand drugs rose from $100.00 to $165.44 between January 2008 and December 2012, the price for an unchanged market basket of generic drugs decreased from $100.00 to $57.38 (in 2008 dollars).

In stark contrast to the dramatic price changes experienced for brand and generic drugs since 2008, inflation as measured by the Consumer Price Index (CPI) across a broad market basket of goods and services—not just prescription drugs—has only fluctuated between 0.1% and 3.0% during the same time period.

Figure 9:
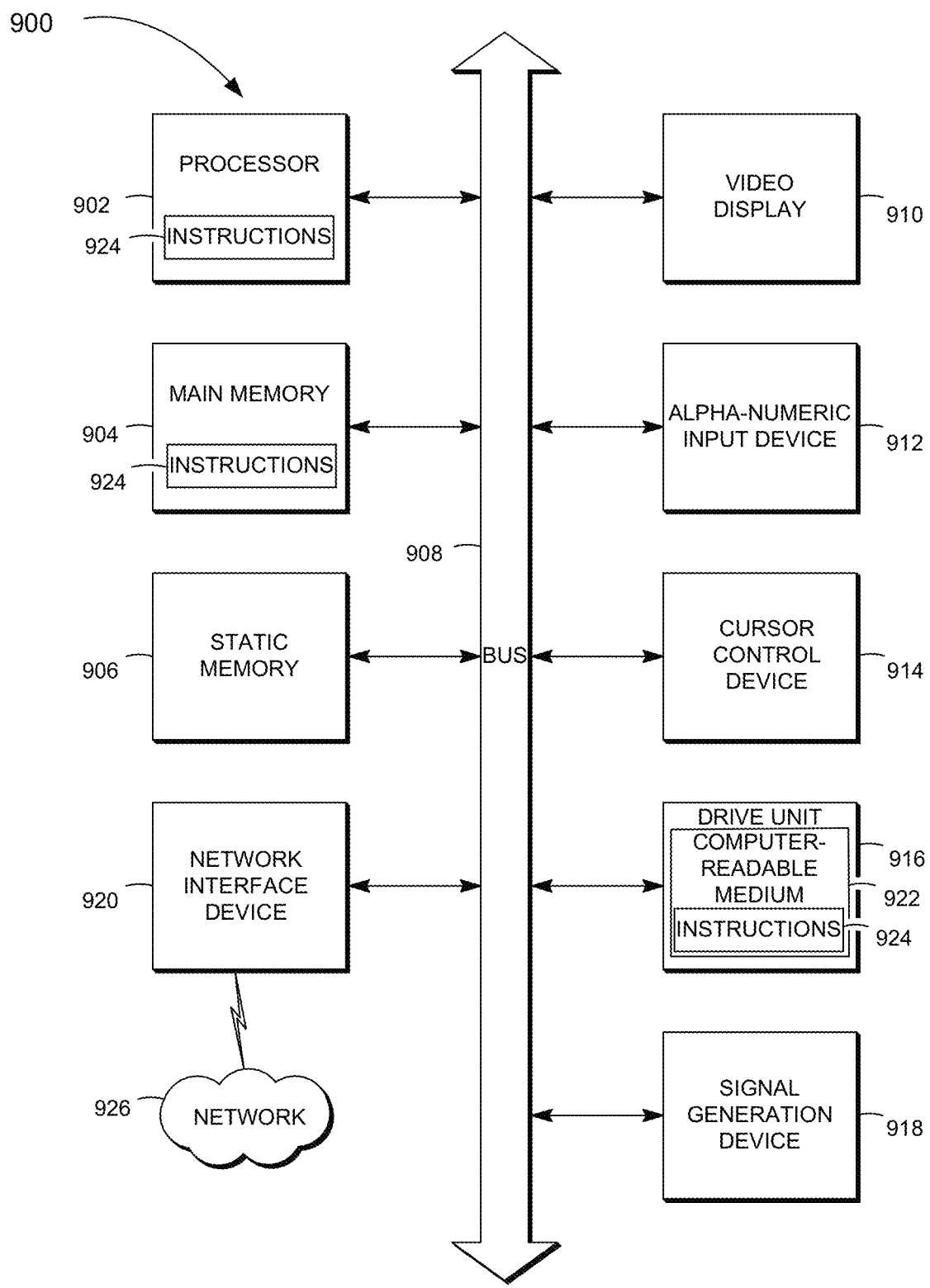
FIG. 9 is a block diagram of a machine in the example form of a computer system within which a set of instructions for causing the machine to perform any one or more of the methodologies discussed herein may be executed or stored.

FIG. 9 shows a block diagram of a machine in the example form of a computer system 900 within which a set of instructions may be executed causing the machine to perform any one or more of the methods, processes, operations, or methodologies discussed herein. The user device 102 and/or the benefit manager device 106 may include the functionality of the one or more computer systems 900.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (e.g., a central processing unit (CPU) a graphics processing unit (GPU) or both), a main memory 904 and a static memory 906, which communicate with each other via a bus 908. The computer system 900 further includes a video display unit 910 (e.g., a liquid crystal display (LCD) or a cathode ray tube (CRT)). The computer system 900 also includes an alphanumeric input device 912 (e.g., a keyboard), a cursor control device 914 (e.g., a mouse), a drive unit 916, a signal generation device 918 (e.g., a speaker) and a network interface device 920.

The drive unit 916 includes a computer-readable medium 922 on which is stored one or more sets of instructions (e.g., software 924) embodying any one or more of the methodologies or functions described herein. The software 924 may also reside, completely or at least partially, within the main memory 904 and/or within the processor 902 during execution thereof by the computer system 900, the main memory 904 and the processor 902 also constituting computer-readable media.

The software 924 may further be transmitted or received over a network 926 via the network interface device 920.

While the computer-readable medium 922 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, an index sample including an identification of a plurality of drugs is selected. A weighting factor associated with each of the plurality of drugs in the index sample is calculated. A first weighted price for the plurality of drugs for a first time period is calculated. A second weighted price for the plurality of drugs for a second time period is calculated. A price index for the second time period is calculated based on the first weighted price and the second weighted price.

In an example embodiment, a trend sample population including a plurality of members one or more of drug benefit plans is selected. Pharmacy claims data associated with each of the plurality of members is accessed. A report metric for first time period is calculated based on the pharmacy claims data. The report metric for a second time period is calculated based on the pharmacy claims data based on the pharmacy claims data.

Thus, methods and systems for determining drug trend and drug inflation have been described. Although embodiments of the inventive subject matter have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

While the methods and systems are generally described as being performed by a PBM, other types of organizations (e.g., with sufficient access to data) may perform the methods and systems described herein.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method for displaying drug indexes relating to insights of various drugs relative to a baseline, comprising:
   electronically receiving, at a benefit manager device storing patient prescription drug data from a user device, a request for a drug price index trend;
   selecting, on a processor of the benefit manager device, an index sample, the index sample including an identification of a plurality of drugs;
   associating, on the processor of the benefit manager device, a weighting factor, which is calculated from a drug utilization of the plurality of drugs, with each of the plurality of drugs in the index sample;
   identifying, on the processor of the benefit manager device, a first weighted price value for the plurality of drugs over a first time period and using the weighting factor corresponding to a particular drug of the plurality of drugs;
   identifying, on the processor of the benefit manager device, a second weighted price value for the plurality of drugs over a second time period and using the weighting factor corresponding to the particular drug of the plurality of drugs;
   determining, on the processor of the benefit manager device, the drug price index trend for the second time period based on the first weighted price value and the second weighted price value using a sampling of members of one or more drug benefit plans;
   modifying the index sample by excluding a drug among the plurality of drugs to create a modified index sample including an identification of a modified set of drugs;
   calculating a first modified weighted price value of the modified set of drugs for the first time period using a modified drug utilization of the modified set of drugs;
   calculating a second modified weighted price value of the modified set of drugs for the second time period using the modified drug utilization of the modified set of drugs;
   calculating an additional weighted price value of the modified set of drugs for a third time period using the modified drug utilization of the modified set of drugs;
   determining a modified price index trend for the second time period based on the first modified weighted price value and the second modified weighted price value for the modified set of drugs;
   calculating a price index trend for the third time period based on the second modified weighted price value and the additional weighted price value for the modified set of drugs;
   transmitting the drug price index trend for at least one of the second time period or the third time period from the processor to the user device; and
   changing a display from a request graphical user interface to a composite display including a first plot of a baseline drug price index trend, a second plot of the price index trend for the second time period, and a third plot of the price index trend for the third time period, each for the modified set of drugs and each free of patient prescription drug data with the display predicting future healthcare utilization.

2. The method of claim 1, further comprising:
   calculating, using the processor of the benefit manager device, a relative utilization for each of the plurality of drugs relative to other drugs in the index sample,
   calculating, using the processor of the benefit manager device, a total number of normalized prescriptions for each drug during the first time period,
   summing, using the processor of the benefit manager device, the normalized prescriptions across the plurality drugs of the index sample; and
   displaying on the composite display the relative utilization and the total number of normalized prescriptions.

3. The method of claim 1, wherein the first weighted price value for the plurality of drugs for the first time period is based on the weighting factor associated with each of the plurality of drugs and a drug cost associated with each of the plurality of drugs for the first time period.

4. The method of claim 1, wherein the second weighted price value for the plurality of drugs for the second time period is based on the weighting factor associated with each of the plurality of drugs and a drug cost associated with each of the plurality of drugs for the second time period.

5. The method of claim 1, further comprising:
   calculating an inflation rate based on a rate of change of the price index trend; and
   displaying the inflation rate on the composite display for both brand drugs and generic drugs.

6. The method of claim 3, wherein the drug cost includes a cost of a drug to be paid to a pharmacy minus rebate paid to a pharmacy benefit manager by a drug supplier.

7. The method of claim 1, wherein modifying the index sample comprises:
   modifying the index sample by including an additional drug to create the modified index sample including the identification of the modified set of drugs; and
   displaying a suggested modification of a drug benefit based on a trend rate of the modified index sample.

8. The method of claim 1, further comprising:
   calculating, using the processor of the benefit manager device, a relative utilization proportion for each of the plurality of drugs relative to other drugs in the index sample,
   calculating, using the processor of the benefit manager device, a total number of normalized prescriptions for a drug during the first time period, and
   summing, using the processor of the benefit manager device, the normalized prescriptions across the plurality drugs of the index sample.

9. A method comprising:
- receiving at a benefit manager device from a user device a request for a report metric trend;
- selecting, on a processor of the benefit manager device, a trend sample population including a plurality of members of one or more of drug benefit plans;
- selecting, on the processor, an index sample, the index sample including an identification of a plurality of drugs;
- accessing, on the processor, pharmacy claims data associated with each of the plurality of members;
- calculating, on the processor, a first report metric trend for a first time period based on the pharmacy claims data including calculating a drug weight as a product of a total number of normalized prescriptions a specific drug of the index sample and an inverted sum of normalized prescriptions across the drugs that constitute the index sample;
- calculating, on the processor, a second report metric trend for a second time period based on the pharmacy claims data;
- modifying the index sample by excluding a drug among the plurality of drugs to create a modified index sample including an identification of a modified set of drugs;
- calculating, on the processor, a modified report metric trend using the modified index sample;
- transmitting a third report metric trend based on the first report metric trend and the second report metric trend and the modified report metric trend from the benefit manager device to the user device; and
- changing a display from a request graphical user interface to the third report metric trend on a composite display at the user device.

10. The method of claim 9, wherein the trend sample population includes the plurality of members of the one or more drug benefit plans during both the first time period and the second time period.

11. The method of claim 9, wherein each report metric includes a drug utilization associated with the plurality of members.

12. The method of claim 11, further comprising normalizing prescription data; and calculating the drug utilization using the normalized prescription data from normalizing step.

13. The method of claim 11, wherein the drug utilization is based on a per-member-per-year basis.

14. The method of claim 11, wherein calculating the first report metric trend includes calculating the drug utilization based on a therapy class.

15. The method of claim 9, wherein the third report metric trend includes a prescription cost metric.

16. The method of claim 9, wherein the first time period includes a time period within a first year, and the second time period includes a corresponding time period within a second year.

17. The method of claim 16, wherein the first time period is a one-month time period.

18. The method of claim 16, wherein the first time period includes a cumulative time period.

19. The method of claim 9, further comprising:
- calculating a trend rate based on the first report metric trend for the first time period and the second report metric trend for the second time period.

20. A non-transitory machine-readable medium comprising instructions, which, when executed by one or more processors, cause the one or more processors to perform the following operations:
- receive at a benefit manager device from a user device a request for a price index trend;
- select, at the benefit manager device, an index sample including an identification of a plurality of drugs;
- calculate, at the benefit manager device, a weighting factor associated with each of the plurality of drugs in the index sample using a drug utilization of the plurality of drugs;
- calculate a first weighted price value for the plurality of drugs for a first time period using a sampling of members of one or more drug benefit plans;
- calculate a second weighted price value for the plurality of drugs for a second time period using the sampling of members of one or more drug benefit plans;
- calculate a first price index trend for the second time period based on the first weighted price value and the second weighted price value;
- modifying the index sample by excluding a drug among the plurality of drugs to create a modified index sample including the identification of a modified set of drugs;
- calculating a first modified weighted price value of the modified set of drugs for the first time period;
- calculating a second modified weighted price value of the modified set of drugs for the second time period;
- calculating an additional weighted price value of the modified set of drugs for a third time period;
- calculating a modified price index trend for the second time period based on the first modified weighted price value and the second modified weighted price value;
- calculating a second price index trend for the third time period based on the second modified weighted price value and the additional weighted price value;
- transmit the first price index trend and the second price index trend from the benefit manager device to the user device; and
- changing from a request graphical user interface to a first plot of the first price index trend and a second plot of the second price index trend on a display on the user device.

21. The method of claim 9, wherein calculating the third report metric trend includes using a weight to calculate the third report metric trend, wherein the weight is calculated with $$w_i = \frac{RX_i}{\sum_{i}^{N} RX_i}$$

wherein "$w_i$" is a weighting factor for drug "i", "$RX_i$" is a total number of normalized prescriptions for drug "i" during the first time period, and $$\sum_{i}^{N} RX_i$$

is a sum of normalized prescriptions across "N" drugs that constitute an index sample.

* * * * *